(12) United States Patent
Mori

(10) Patent No.: US 8,367,724 B2
(45) Date of Patent: Feb. 5, 2013

(54) ESTER COMPOUND AND USE THEREOF

(75) Inventor: Tatsuya Mori, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 115 days.

(21) Appl. No.: 12/947,852

(22) Filed: Nov. 17, 2010

(65) Prior Publication Data

US 2011/0065789 A1 Mar. 17, 2011

Related U.S. Application Data

(62) Division of application No. 12/528,528, filed as application No. PCT/JP2008/053884 on Feb. 27, 2008, now Pat. No. 7,968,598.

(30) Foreign Application Priority Data

Feb. 28, 2007 (JP) .................................. 2007-048936
Oct. 3, 2007 (JP) .................................. 2007-259566

(51) Int. Cl.
*A01N 37/34* (2006.01)
*A01N 53/02* (2006.01)
*C07C 255/31* (2006.01)

(52) U.S. Cl. .................. 514/521; 514/531; 558/426

(58) Field of Classification Search ................... 558/426
See application file for complete search history.

(56) References Cited

U.S. PATENT DOCUMENTS

| 4,405,640 | A | 9/1983 | Punja |
| 5,135,951 | A | 8/1992 | Babin et al. |
| 6,908,945 | B2 * | 6/2005 | Mori ............................. 514/521 |
| 7,968,598 | B2 | 6/2011 | Mori |
| 2003/0195119 | A1 | 10/2003 | Mori |

FOREIGN PATENT DOCUMENTS

| CN | 1451650 A | 10/2003 |
| EP | 0 448 427 A1 | 9/1991 |
| EP | 0 926 129 A1 | 6/1999 |
| EP | 1 462 441 A1 | 9/2004 |
| WO | 2007/083781 A1 | 7/2007 |

OTHER PUBLICATIONS

Int'l Search Report issued on Jul. 4, 2008 in Int'l Application No. PCT/JP2008/053884.
Int'l Preliminary Report on Patentability issued on Sep. 1, 2009 in Int'l Application No. PCT/JP2008/053884.
Office Action issued May 15, 2012 in CN Application No. 200880013693.0.
Office Action issued Jun. 15, 2012 in MY Application No. PI 20093539.
Office Action Issued Sep. 16, 2010 in U.S. Appl. No. 12/528,528.
Office Action issued Aug. 1, 2011 in RU Application No. 2009135804.

* cited by examiner

*Primary Examiner* — Shawquia Young
(74) *Attorney, Agent, or Firm* — Panitch Schwarze Belisario & Nadel LLP

(57) ABSTRACT

An ester compound represented by the formula (1):

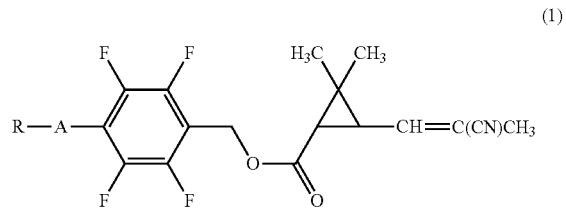

wherein R represents a C1-C4 alkyl group or a C3-C4 alkenyl group, and A represents a single bond or an oxygen atom, has an excellent pest controlling efficacy, and it is useful as an active ingredient of a pest controlling agent.

9 Claims, No Drawings

ESTER COMPOUND AND USE THEREOF

CROSS-REFERENCE TO RELATED APPLICATIONS

This application is a divisional of co-pending U.S. patent application Ser. No. 12/528,528, filed Aug. 25, 2009, which is a Section 371 of International Application No. PCT/JP2008/053884, filed Feb. 27, 2008, which was published in the English language on Sep. 12, 2008 under International Publication No. WO 2008/108376 A1, and the disclosure of which is incorporated herein by reference.

BACKGROUND OF THE INVENTION

The present invention relates to an ester compound and use thereof.

EP 0926129 A1 describes a certain kind of tetrafluorobenzyl ester compounds.

BRIEF SUMMARY OF THE INVENTION

An object of the present invention is to provide a compound having an excellent pest controlling efficacy.

The present inventor has intensively studied in order to find out a compound having an excellent pest controlling efficacy and, as a result, found out that a compound represented by the formula (1) hereinafter has an excellent pest controlling efficacy, leading to the present invention.

That is, the present invention is to provide:
1. An ester compound represented by the formula (1):

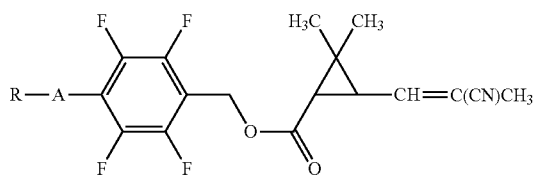

(1)

wherein R represents a C1-C4 alkyl group or a C3-C4 alkenyl group, and A represents a single bond or an oxygen atom (hereinafter referred to as present compound;
2. The ester compound according to the above 1, wherein A is a single bond;
3. The ester compound according to the above 1, wherein A is an oxygen atom;
4. A pest controlling agent comprising the ester compound represented by the formula (1) as an active ingredient;
5. A method of controlling pests comprising applying an effective amount of the ester compound represented by the formula (1) to pests or a place where pests inhabit; and
6. Use of the ester compound represented by the formula (1) for controlling pests.

Since the present compound has an excellent pest controlling efficacy, it is useful as an active ingredient of a pest controlling agent.

DETAILED DESCRIPTION OF THE INVENTION

In the present compound, there are isomers resulted from two asymmetric carbon atoms present on the cyclopropane ring, and isomers resulted from the double bond, and each of them and a mixture of these isomers having an arbitrary ratio are included in the present invention.

In the present invention, examples of the C1-C4 alkyl group include a methyl group, an ethyl group, a propyl group and the like, and examples of the C3-C4 alkenyl group include an allyl group.

Examples of the present compound include the following compounds:

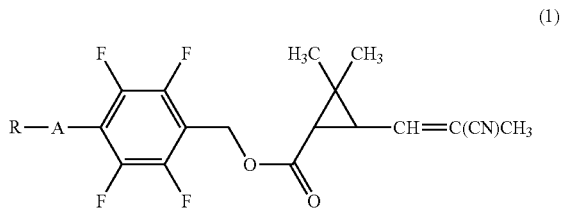

(1)

A compound represented by the formula (1) in which an absolute configuration of the 1-position of the cyclopropane ring is an R configuration;

A compound represented by the formula (1) in which a relative configuration of the substituent at the 1-position of the cyclopropane ring and the substituent at the 3-position of the cyclopropane ring is a trans configuration;

A compound represented by the formula (1) in which a relative configuration of the substituent at the 1-position of the cyclopropane ring and the substituent at the 3-position of the cyclopropane ring is a cis configuration;

A compound represented by the formula (1) in which a relative configuration of the double bond present on the substituent at the 3-position of the cyclopropane ring is a Z configuration;

A compound represented by the formula (1) in which an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) in which an absolute configuration of the 1-position of the cyclopropane ring is R configuration, and a relative configuration of the substituent at the 1-position of the cyclopropane ring and the substituent at the 3-position of the cyclopropane ring is a cis configuration;

A compound represented by the formula (1) in which an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the double bond present on the substituent at the 3-position of the cyclopropane ring is a Z configuration;

A compound represented by the formula (1) in which an absolute configuration of the 1-position of the cyclopropane ring is an R configuration, a relative configuration of the substituent at the 1-position of the cyclopropane ring and the substituent at the 3-position of the cyclopropane ring is a cis configuration, and a relative configuration of the double bond present on the substituent at the 3-position of the cyclopropane ring is a Z configuration;

A compound represented by the formula (1) rich in a compound in which an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1), containing not less than 80% of which is a compound in which an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1), containing not less than 90% of which is a compound in which an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) in which R is a C1-C4 alkyl group;

A compound represented by the formula (1) in which R is a C3-C4 alkenyl group;

A compound represented by the formula (1) in which R is a methyl group or an allyl group;

A compound represented by the formula (1) in which A is a single bond;

A compound represented by the formula (1) in which A is an oxygen atom;

A compound represented by the formula (1) in which R is a C1-C4 alkyl group, and A is a single bond;

A compound represented by the formula (1) in which R is a C1-C4 alkyl group, A is a single bond, and an absolute configuration of the 1-position of the cyclopropane ring is an R configuration;

A compound represented by the formula (1) in which R is a C1-C4 alkyl group, A is a single bond, and a relative configuration of the substituent at the 1-position of the cyclopropane ring and the substituent at the 3-position of the cyclopropane ring is a trans configuration;

A compound represented by the formula (1) in which R is a C1-C4 alkyl group, A is a single bond, and a relative configuration of the substituent at the 1-position of the cyclopropane ring and the substituent at the 3-position of the cyclopropane ring is a cis configuration;

A compound represented by the formula (1) in which R is a C1-C4 alkyl group, A is a single bond, and a relative configuration of the double bond present on the substituent at the 3-position of the cyclopropane ring is a Z configuration;

A compound represented by the formula (1) in which R is a C1-C4 alkyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound in which R is a C1-C4 alkyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a cis configuration;

A compound represented by the formula (1) in which R is a C1-C4 alkyl group, A is a single bond, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the double bond present on the substituent at the 3-position of the cyclopropane ring is a Z configuration;

A compound represented by the formula (1) in which R is a C1-C4 alkyl group, A is a single bond, an absolute configuration of the 1-position of the cyclopropane ring is an R configuration, a relative configuration of the substituent at the 1-position of the cyclopropane ring and the substituent at the 3-position of the cyclopropane ring is a cis configuration, and a relative configuration of the double bond present on the substituent at the 3-position of the cyclopropane ring is Z configuration;

A compound represented by the formula (1) rich in a compound in which R is a C1-C4 alkyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound containing represented by the formula (1), containing not less than 80% of which is a compound in which R is a C1-C4 alkyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1), containing not less than 90% of which is a compound in which R is a C1-C4 alkyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) in which R is a C3-C4 alkenyl group, and A is a single bond;

A compound represented by the formula (1) in which R is a C3-C4 alkenyl group, A is a single bond, and an absolute configuration of the 1-position of the cyclopropane ring is an R configuration;

A compound represented by the formula (1) in which R is a C3-C4 alkenyl group, A is a single bond, and a relative configuration of the substituent at the 1-position of the cyclopropane ring and the substituent at the 3-position of the cyclopropane ring is a trans configuration;

A compound represented by the formula (1) in which R is a C3-C4 alkenyl group, A is a single bond, and an relative configuration of the substituent at the 1-position of the cyclopropane ring and the substituent at the 3-position of the cyclopropane ring is a cis configuration;

A compound represented by the formula (1) in which R is a C3-C4 alkenyl group, A is a single bond, and a relative configuration of the double bond present on the substituent at the 3-position of the cyclopropane ring is a Z configuration;

A compound represented by the formula (1) in which R is a C3-C4 alkenyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) in which R is a C3-C4 alkenyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a cis configuration;

A compound represented by the formula (1) in which R is a C3-C4 alkenyl group, A is a single bond, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the double bond present on the substituent at the 3-position of the cyclopropane ring is a Z configuration;

A compound represented by the formula (1) in which R is a C3-C4 alkenyl group, A is a single bond, an absolute configuration of the 1-position of the cyclopropane ring is an R configuration, a relative configuration of the substituent at the 1-position of the cyclopropane ring and the substituent at the 3-position of the cyclopropane ring is a cis configuration, and a relative configuration of the double bond present on the substituent at the 3-position of the cyclopropane ring is a Z configuration;

A compound represented by the formula (1) rich in a compound in which R is a C3-C4 alkenyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) containing not less than 80% of which is a compound in which R is a C3-C4 alkenyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) containing not less than 90% of which is a compound in which R is a C3-C4 alkenyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) in which R is a C1-C4 alkyl group, and A is an oxygen atom;

A compound represented by the formula (1) in which R is a C1-C4 alkyl group, A is an oxygen atom, and an absolute configuration of the 1-position of the cyclopropane ring is an R configuration;

A compound represented by the formula (1) in which R is a C1-C4 alkyl group, A is an oxygen atom, and a relative configuration of the substituent at the 1-position of the cyclopropane ring and the substituent at the 3-position of the cyclopropane ring is a trans configuration;

A compound represented by the formula (1) in which R is a C1-C4 alkyl group, A is an oxygen atom, and a relative configuration of the substituent at the 1-position of the cyclopropane ring and the substituent at the 3-position of the cyclopropane ring is a cis configuration;

A compound represented by the formula (1) in which R is a C1-C4 alkyl group, A is an oxygen atom, and a relative configuration of the double bond present on the substituent at the 3-position of the cyclopropane ring is a Z configuration;

A compound represented by the formula (1) in which R is a C1-C4 alkyl group, A is an oxygen atom, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) in which R is a C1-C4 alkyl group, A is an oxygen atom, an absolute configuration of the 1-position of the cyclopropane ring is an R configuration, and a relative configuration of the substituent at the 1-position of the cyclopropane ring and the substituent at the 3-position of the cyclopropane ring is a cis configuration;

A compound represented by the formula (1) in which R is a C1-C4 alkyl group, A is an oxygen atom, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the double bond present on the substituent at the 3-position of the cyclopropane ring is a Z configuration;

A compound represented by the formula (1) in which R is a C1-C4 alkyl group, A is an oxygen atom, an absolute configuration of the 1-position of the cyclopropane ring is an R configuration, a relative configuration of the substituent at the 1-position of the cyclopropane ring and the substituent at the 3-position of the cyclopropane ring is a cis configuration, and a relative configuration of the double bond present on the substituent at the 3-position of the cyclopropane ring is a Z configuration;

A compound represented by the formula (1) rich in a compound in which R is a C1-C4 alkyl group, A is an oxygen atom, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) containing not less than 80% of which is a compound in which R is a C1-C4 alkyl group, A is an oxygen atom, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) containing not less than 90% of which is a compound in which R is a C1-C4 alkyl group, A is an oxygen atom, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) in which R is a methyl group, and A is a single bond;

A compound represented by the formula (1) in which R is a methyl group, A is a single bond, and an absolute configuration of the 1-position of the cyclopropane ring is an R configuration;

A compound represented by the formula (1) in which R is a methyl group, A is a single bond, and a relative configuration of the substituent at the 1-position of the cyclopropane ring and the substituent at the 3-position of the cyclopropane ring is a trans configuration;

A compound represented by the formula (1) in which R is a methyl group, A is a single bond, and a relative configuration of the substituent at the 1-position of the cyclopropane ring and the substituent at the 3-position of the cyclopropane ring is a cis configuration;

A compound represented by the formula (1) in which R is a methyl group, A is a single bond, and a relative configuration of the double bond present on the substituent at the 3-position of the cyclopropane ring is a Z configuration;

A compound represented by the formula (1) in which R is a methyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) in which R is a methyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a cis configuration;

A compound represented by the formula (1) in which R is a methyl group, A is a single bond, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the double bond present on the substituent at the 3-position of the cyclopropane ring is a Z configuration;

A compound represented by the formula (1) in which R is a methyl group, A is a single bond, an absolute configuration of the 1-position of the cyclopropane ring is an R configuration, a relative configuration of the substituent at the 1-position of the cyclopropane ring and the substituent at the 3-position of the cyclopropane ring is a cis configuration, and a relative configuration of the double bond present on the substituent at the 3-position of the cyclopropane ring is a Z configuration;

A compound represented by the formula (1) rich in a compound in which R is a methyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) containing not less than 80% of which is a compound in which R is a methyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) containing not less than 90% of which is a compound in which R is a methyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) in which R is an allyl group, and A is a single bond;

A compound represented by the formula (1) in which R is an allyl group, A is a single bond, and an absolute configuration of the 1-position of the cyclopropane ring is an R configuration;

A compound represented by the formula (1) in which R is an allyl group, A is a single bond, and a relative configuration of the substituent at the 1-position of the cyclopropane ring and the substituent at the 3-position of the cyclopropane ring is a trans configuration;

A compound represented by the formula (1) in which R is an allyl group, A is a single bond, and a relative configuration of the substituent at the 1-position of the cyclopropane ring and the substituent at the 3-position of the cyclopropane ring is a cis configuration;

A compound represented by the formula (1) in which R is an allyl group, A is a single bond, and a relative configuration of the double bond present on the substituent at the 3-position of the cyclopropane ring is a Z configuration;

A compound represented by the formula (1) in which R is an allyl group, A is a single bond, an absolute configuration of the 1-position of the cyclopropane ring is an R configuration, and a relative configuration of the substituent at the 1-position of the cyclopropane ring and the substituent at the 3-position of cyclopropane ring is a trans configuration;

A compound represented by the formula (1) in which R is an allyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a cis configuration;

A compound represented by the formula (1) in which R is an allyl group, A is a single bond, an absolute configuration of the 1-position of the cyclopropane ring is an R configuration, a relative configuration of the substituent at the 1-position of the cyclopropane ring and the substituent at the 3-position of the cyclopropane ring is a trans configuration, and a relative configuration of the double bond present on the substituent at the 3-position of the cyclopropane ring is a Z configuration;

A compound represented by the formula (1) in which R is an allyl group, A is a single bond, an absolute configuration of the 1-position of the cyclopropane ring is an R configuration, a relative configuration of the substituent at the 1-position of the cyclopropane ring and the substituent at the 3-position of the cyclopropane ring is a cis configuration, and a relative configuration of the double bond present on the substituent at the 3-position of the cyclopropane ring is a Z configuration;

A compound represented by the formula (1) rich in a compound in which R is an allyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) containing not less than 80% of which is a compound in which R is an allyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) containing not less than 90% of which is a compound in which R is an allyl group, A is a single bond, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) in which R is a methyl group, and A is an oxygen atom;

A compound represented by the formula (1) in which R is a methyl group, A is an oxygen atom, and an absolute configuration of the 1-position of the cyclopropane ring is an R configuration;

A compound represented by the formula (1) in which R is a methyl group, A is an oxygen atom, and a relative configuration of the substituent at the 1-position of the cyclopropane ring and the substituent at the 3-position of the cyclopropane ring is a trans configuration;

A compound represented by the formula (1) in which R is a methyl group, A is an oxygen atom, and a relative configuration of the substituent at the 1-position of the cyclopropane ring and the substituent at the 3-position of the cyclopropane ring is a cis configuration;

A compound represented by the formula (1) in which R is a methyl group, A is an oxygen atom, and a relative configuration of the double bond present on the substituent at the 3-position of the cyclopropane ring is a Z configuration;

A compound represented by the formula (1) in which R is a methyl group, A is an oxygen atom, an absolute configuration of the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) in which R is a methyl group, A is an oxygen atom, an absolute configuration of the 1-position of the cyclopropane ring is an R configuration, and a relative configuration of the substituent at the 1-position of the cyclopropane ring and the substituent at the 3-position of the cyclopropane ring is a cis configuration;

A compound represented by the formula (1) in which R is a methyl group, A is an oxygen atom, an absolute configuration of the 1-position of the cyclopropane ring is an R configuration, a relative configuration of the substituent at the 1-position of the cyclopropane ring and the substituent at the 3-position of a cyclopropane ring is a trans configuration, and a relative configuration of the double bond present on the substituent at the 3-position of the cyclopropane ring is a Z configuration;

A compound represented by the formula (1) in which R is a methyl group, A is an oxygen atom, an absolute configuration of the 1-position of the cyclopropane ring is an R configuration, a relative configuration of the substituent at the 1-position of the cyclopropane ring and the substituent at the 3-position of the cyclopropane ring is a cis configuration, and a relative configuration of the double bond present on the substituent at the 3-position of the cyclopropane ring is a Z configuration;

A compound represented by the formula (1) rich in a compound in which R is a methyl group, A is an oxygen atom, an absolute configuration at the 1-position of the cyclopropane ring is an R configuration, and a relative configuration of the substituent at the 1-position of the cyclopropane ring and the substituent at the 3-position of the cyclopropane ring is a trans configuration;

A compound represented by the formula (1) containing not less than 80% of which is a compound in which R is a methyl group, A is an oxygen atom, an absolute configuration at the 1-position of the cyclopropane ring is an R configuration, and a relative configuration of the substituent at the 1-position of the cyclopropane ring and the substituent at the 3-position of the cyclopropane ring is a trans configuration; and A compound represented by the formula (1) containing not less than 90% of which is a compound in which R is a methyl group, A is an oxygen atom, an absolute configuration at the 1-position of the cyclopropane ring is an R configuration, and a relative configuration of the substituent at the 1-position of the cyclopropane ring and the substituent at the 3-position of the cyclopropane ring is a trans configuration.

The present compound can be produced, for example, by the following process.

A process which comprises reacting an alcohol compound represented by the formula (2):

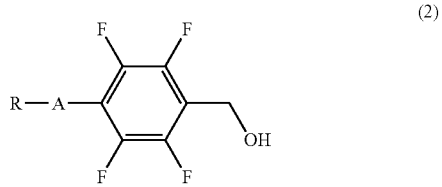

(2)

wherein R represents a C1-C4 alkyl group or a C3-C4 alkenyl group, and A represents a single bond or an oxygen atom, with a carboxylic acid compound represented by the formula (3):

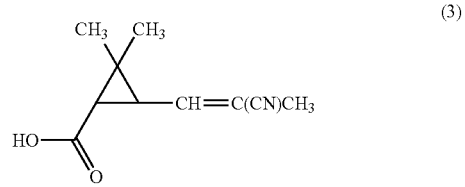

(3)

or a reactive derivative thereof (e.g. acid halide, acid anhydride, etc.).

Usually, this reaction is carried out in a solvent in the presence of a condensing agent or a base.

Examples of the condensing agent include dicyclohexylcarbodiimide and 1-(3-dimethylaminopropyl)-3-ethylcarbodiimide hydrochloride.

Examples of the base include organic bases such as triethylamine, pyridine, N,N-diethylaniline, 4-dimethylaminopyridine, and diisopropylethylamine.

Examples of the solvent include hydrocarbons such as benzene, toluene and hexane, ethers such as diethyl ether and tetrahydrofuran, and halogenated hydrocarbons such as dichloromethane, 1,2-dichloroethane and chlorobenzene.

The reaction time is usually in a range of 5 minutes to 72 hours.

The reaction temperature is usually in a range of −20° C. to 100° C. (provided that, when a boiling point of a solvent used is lower than 100° C., −20° C. to the boiling point of the solvent), preferably in a range of −5° C. to 100° C. (provided that, when a boiling point of a solvent used is lower than 100° C., −5° C. to the boiling point of the solvent).

In the reaction, a mole ratio of the alcohol compound represented by the formula (2), and the carboxylic acid compound represented by the formula (3) or a reactive derivative thereof to be used can be appropriately selected, but the reaction is preferably carried out at an equal mole ratio or a ratio near to it.

Usually, the condensing agent or the base can be used in an appropriate ratio of 1 mole to an excessive amount, preferably 1 mole to 5 moles relative to 1 mole of the alcohol compound represented by the formula (2). The condensing agent or the base is appropriately selected depending on a kind of a particular carboxylic acid compound represented by the formula (3) or a reactive derivative thereof (e.g. corresponding acid chloride compound, acid bromide compound, acid anhydride, etc. of the carboxylic acid compound represented by the formula (3)).

After completion of the reaction, the reaction mixture is subjected to a conventional post-treatment procedure, for example, filtering the reaction mixture followed by concentrating the resulting filtrate, or pouring the reaction mixture into water followed by extraction with an organic solvent and concentration of the extract to obtain the present compound. The resulting present compound can be purified by a conventional procedure such as chromatography and distillation.

The alcohol compound represented by the formula (2) is a commercially available product, or a compound described in EP 0926129 A1 and U.S. Pat. No. 4,405,640, and can be purchased as a commercially available product, or can be produced by the method described in these publications.

The carboxylic acid compound represented by the formula (3) is a compound described, for example, in Agr. Biol. Chem., 34, 1119 (1970), and can be produced by the method described therein.

Examples of pests on which the present compound has efficacy include arthropods such as insects and acarines, specifically, for example, the following pests.

Lepidoptera:

Pyralidae such as *Chilo suppressalis* (rice stem borer), *Cnaphalocrocis medinalis* (rice leafroller), *Plodia interpunctella* (Indian meal moth) and the like; Noctuidae such as *Spodoptera litura* (common cutworm), *Pseudaletia separate* (rice armyworm), *Mamestra brassicae* (cabbage armyworm) and the like; Pieridae such as *Pieris rapae* (common cabbageworm) and the like; Tortricidae such as *Adoxophyes orana* and the like;

Carposinidae; Lyonetiidae; Lymantriidae; Plusiinae; *Agrotis* ssp. such as *Agrotis segetum* (cutworm), *Agrotis ipsilon* (black cutworm) and the like; *Helicoverpa* spp.; *Heliothis* spp.; *Plutella xylostella* (diamondback moth); *Parnara guttata* (rice skipper); *Tinea pellionella* (casemaking clothes moth); *Tineola bisselliell* (webbing clothes moth); and the like;

Diptera:

Calicidae such as *Culex pipiens pallens* (common mosquito), *Culex tritaeniorhynchus* and the like; *Aedes* spp. such as *Aedes aegypti, Aedes albopictus* and the like; *Anopheles* spp. such as *Anopheles sinensis* and the like; Chironomidae (midges); Muscidae such as *Musca domestica* (housefly), *Muscina stabulans* (false stablefly), *Fannia canicularis* (lesser housefly) and the like; Calliphordiae; Sarcophagidae; Anthomyiidae such as *Hylemya platura* (seedcorn maggot), *Delia antique* (onion maggot) and the like; Tephritidae (fruit flies); Drosophilidae (small fruit flies); Psychodidae (moth flies); Phoridae; Simuliidae (black flies); Tabanidae; Stomoxyidae (stable flies); Ceratopogonidae; and the like;

Dictyoptera:

*Blattella germanica* (German cockroach), *Periplaneta fuliginosa* (smokybrown cockroach), *Periplaneta americana* (American cockroach), *Periplaneta brunnea* (brown cockroach), *Blatta orientalis* (oriental cockroach) and the like;

Hymenoptera:

Formicidae (Ants); Vespidae (hornets); Bethylidae; Tenthredinidae such as *Athalia rosae japonensis* (cabbage sawfly) and the like;

Aphaniptera:

*Ctenocephalides canis, Ctenocephalides felis, Pulex irritans* and the like;

Anoplura:

*Pediculus humanus, Phthirus pubis, Pediculus humanus humanus, Pediculus humanus corporis* and the like;

Isoptera:

*Reticulitermes speratus, Coptotermes formosanus* and the like;

Hemiptera:

Delphacidae (planthoppers) such as *Laodelphax striatellus* (small brown planthopper), *Nilaparvata lugens* (brown rice planthopper), *Sogatella furcifera* (white-backed rice planthopper) and the like; Deltocephalidae (leafhoppers) such as *Nephotettix cincticeps* (green rice leafhopper), *Nephotettix virescens* (green rice leafhopper) and the like; Aphididae (aphids); Pentatomidae (stink bugs); Aleyrodidae (whiteflies); Coccidae (scales); Tingidae (lace bugs); Psyliidae (psyllids) and the like;

Coleoptera:

*Attagenus japonicus; Anthrenus verbasci; Diabrotica* spp. (corn rootworms) such as *Diabrotica virgifera* (western corn rootworm), *Diabrotica undecimpunctata howardi* (southern corn rootworm) and the like; Scarabaeidae such as *Anomala cuprea* (cupreous chafer), *Anomala rufocuprea* (soybeans beetle) and the like; Curculionidae such as *Sitophilus zeamais* (maize weevil), *Lissorhoptrus oryzophilus* (rice water weevil), *Anthonomus gradis grandis* (cottonseed weevil), *Callosobruchuys chienensis* (adzuki been weevil) and the like; Tenebrionidae (darkling beetles) such as *Tenebrio molitor* (yellow mealworm), *Tribolium castaneum* (red flour beetle) and the like; Chrysomelidae (leaf beetles) such as *Oulema oryzae* (rice leaf beetle), *Phyllotreta striolata* (striped flea beetle), *Aulacophora femoralis* (cucurbit leaf beetle) and the like; Anobiidae (drugstore beetles); *Epilachna* spp. such as *Epilachna vigintioctopunctata* (twenty-eight-spotted ladybird) and the like; Lyctidae (powder post beetles); Bostrychidae (false powder post beetles); Cerambycidae (longhorn beetles); *Paederus fuscipes* (rove beetles); and the like;

Thysanoptera:

*Thrips palmi, Frankliniella occidentalis, Thrips hawaiiensis* (flower thrips) and the like;

Orthoptera:

*Gryllotalpa fossor* Scudder, Acrididae (grasshopper) and the like;

Acarina:

Dermanyssidae such as *Dermatophagoides farinae, Dermatophagoides ptrenyssnus* and the like; Acaridae such as *Tyrophagus putrescentiae* (mold mite), *Aleuroglyphus ovatus* (brown legged grain mite) and the like; Glycyphagidae such as *Glycyphagus privates, Glycyphagus domesticus, Glycyphagus destructor* (groceries mite) and the like; Cheyletidae such as *Cheyletus malaccensis, Cheyletus malaccesis* and the like; Tarsonemidae; Chortoglyphidae; Haplochthoniidae; Tetranychidae such as *Tetranychus urticae* (two-spotted spider mite), *Tetranychus kanzawai* (Kanzawa spider mite), *Panonychus citri* (citrus red mite), *Panonychus ulmi* (European red mite) and the like; Ixodidae such as *Haemaphysalis longicornis* and the like.

The pest controlling agent of the present invention may be the present compound itself or, usually, it is formulation comprising the present compound and an inert carrier.

Examples of the formulation include oil solutions, emulsifiable concentrates, wettable powders, flowables formulations (e.g. aqueous suspension, aqueous emulsion), dusts, granules, aerosols, volatile formulations by heating (e.g. insecticidal coil, insecticidal mat for electric heating, volatile formulations with absorptive wick for heating), heating fumigants (e.g. self burning-type fumigants, chemical reaction-type fumigants, porous ceramic plate fumigants etc.), non-heating volatile formulations (e.g. resin volatile formulations, impregnated paper volatile formulations), smoking formulations (e.g. fogging), ULV formulations and poisonous baits.

Examples of a method of formulation include the following methods.

[1] A method of mixing the present compound with a solid carrier, a liquid carrier, a gaseous carrier, a bait or the like and, if necessary, adding a surfactant and other auxiliaries for a formulation.

[2] A method of impregnating a shaped solid carrier not containing an active ingredient with the present compound.

[3] A method of mixing the present compound with a powdery solid carrier, and optionally adding a surfactant and other auxiliaries for a formulation, followed by shaping the resulting mixture.

These formulations contain the present compound at a weight ratio of usually 0.001 to 95% depending on a formulation type.

Examples of the carrier used for formulation include solid carriers {clays (e.g. kaolin clay, diatomaceous earth, synthetic hydrous silicon oxide, bentonite, Fubasami clay and acid clay), talcs, ceramics, other inorganic minerals (e.g. sericite, quartz, sulfur, active carbon, calcium carbonate, hydrated silica and montmorillonite), chemical fertilizers (e.g. ammonium sulfate, ammonium phosphate, ammonium nitrate, urea and ammonium chloride) etc.}; liquid carriers {water, alcohols (e.g. methanol and ethanol), ketones (e.g. acetone and methyl ethyl ketone), aromatic hydrocarbons (e.g. benzene, toluene, xylene, ethylbenzene, methylnaphthalene and phenylxylylethane), aliphatic hydrocarbons (e.g. hexane, cyclohexane, kerosene and gas oil), esters (e.g. ethyl acetate and butyl acetate), nitriles (e.g. acetonitrile and isobutyronitrile), ethers (e.g. diisopropyl ether and dioxane), acid amides (e.g. N,N-dimethylformamide and N,N-dimethylacetamide), halogenated hydrocarbons (dichloromethane, trichloroethane and carbon tetrachloride), dimethyl sulfoxide, vegetable oils (e.g. soybean oil and cottonseed oil) etc.}; and gaseous carriers {flon gas, butane gas, LPG (liquefied petroleum gas), dimethyl ether, carbon dioxide gas etc.}.

Examples of the surfactant include alkylsulfate esters, alkylsulfonate salts, alkylarylsulfonate salts, alkyl aryl ethers, polyoxyethylenated alkyl aryl ethers, polyethylene glycol ethers, polyhydric alcohol esters and sugar alcohol derivatives.

Examples of the other auxiliaries for a formulation include binders, dispersants and stabilizers, for example, casein, gelatin, polysaccharides (e.g. starch, gum arabic, cellulose derivatives and arginic acid), lignin derivatives, bentonite, synthetic water-soluble polymers (e.g. polyvinyl alcohol and polyvinylpyrrolidone), polyacrylic acid, BHT (2,6-di-t-butyl-4-methyphenol), and BHA (a mixture of 2-t-butyl-4-methoxyphenol and 3-t-butyl-4-methoxyphenol).

Examples of the solid carrier for the insecticidal coil include a mixture of a plant powder such as a wooden powder, and Pyrethrum marc and the like, and a binder such as Tabu powder (powder of Machilus thunbergii), starch, gluten, and the like.

Examples of the shaped solid carrier for the insecticidal mat for electric heating include cotton linter formulated into a plate, and a fibril of a mixture of cotton linter and pulp formulated into a plate.

Examples of the solid carrier for the self burning-type fumigant include a burning heat-producing agent such as nitrate, nitrite, guanidine salt, potassium chlorate, nitrocellulose, ethylcellulose, wooden powder, and the like, thermal decomposition stimulating agents such as alkali metal salt, alkaline earth metal salt, bichromate salt, chromate salt, and the like, oxygen supplying agents such as potassium nitrate, and the like, burning assisting agents such as melamine, wheat starch, and the like, bulking agents such as diatomaceous earth, and binders such as synthetic paste, and the like.

Examples of the solid carrier for the chemical reaction-type fumigant include heat producing agents such as sulfide of alkali metal, polysulfide, hydrosulfide, calcium oxide and the like, catalytic agents such as carbonaceous substance, iron carbide, activated clay and the like, organic foaming agents such as azodicarbonamide, benzenesulfonylhydrazide, dinitropentamethylenetetramine, polystyrene, polyurethane and the like, and fillers such as natural fiber pieces, synthetic fiber pieces, and the like.

Examples of the solid carrier for the non-heating volatile formulation include a thermoplastic resin, and a paper (filter paper, Japanese paper, etc.).

Examples of the base material for the poisonous bait include bait ingredients such as cereal powder, vegetable oil, sugar, crystalline cellulose, and the like, antioxidants such as dibutylhydroxytoluene, nordihydroguaiaretic acid, and the like, preservatives such as dehydroacetic acid, and the like, erroneous eating preventing agents for children or pets such as red pepper powder, and pest attracting flavorants such as cheese flavorant, onion flavorant, peanut oil, and the like.

The method of controlling pests of the present invention is usually performed by applying an effective amount of the present compound in a form of the pest controlling agent of the present invention to pests or the place where pests inhabit.

Examples of the method of applying the pest controlling agent of the present invention include the following methods, and the method can be appropriately selected depending on a particular form, a particular use place, and the like, of the pest controlling agent of the present invention.

[1] A method of treating pests or a place where pests inhabit with the pest controlling agent of the present invention as it is.

[2] A method of diluting the pest controlling agent of the present invention with a solvent such as water and the like and, thereafter, spraying this dilute solution to pests or a place where pests inhabit.

In this case, the pest controlling agent of the present invention which has been usually formulated such as emulsifiable concentrates, wettable powders, flowables, microcapsules and the like is diluted to a concentration of 0.1 to 10000 ppm.

[3] A method of heating the pest controlling agent of the present invention at a place where pests inhabit to volatile an active ingredient.

In this case, all of an application amount and an application concentration of the present compound can be appropriately determined depending on a form of the pest controlling agent of the present invention, an application time, an application place, an application method, a kind of pests, damage circumstance, and the like.

The pest controlling agent of the present invention can be mixed with or can be used with other insecticide, nematocide, soil pest controlling agent, fungicide, herbicide, plant growth regulating agent, repellent, synergist, fertilizer, or soil modifier.

Examples of an active ingredient of such the insecticide and acaricide include organic phosphorus compounds such as fenitrothion, fenthion, diazinon, chlorpyrifos, acephate, methidathion, disulfoton, DDVP, sulprofos, cyanophos, dioxabenzofos, dimethoate, phenthoato, malathion, trichlorfon, azinphos-methyl, monocrotophos, ethion, and the like;

carbamate compounds such as BPMC, benfuracarb, propoxur, carbosulfan, carbaryl, methomyl, ethiofencarb, aldicarb, oxamyl, fenothiocarb, and the like;

pyrethroid compounds such as etofenprox, fenvalerate, esfenvalerate, fenpropathrin, cypermethrin, permethrin, cyhalothrin, deltamethrin, cycloprothrin, fulvalinate, biphenthrine, 2-methyl-2-(4-bromodifluoromethoxyphenyl) propyl (3-phenoxybenzyl)ether, tralomethrin, silafluofen, d-phenothrin, cyphenothrine, d-resmethrin, acrinathrin, cyfluthrin, tefluthrin, transfluthrin, tetramethrin, allethrin, d-furamethrin, prallethrin, empenthrin, 5-(2-propynyl)furfuryl 2,2,3,3-tetramethylcyclopropanecarboxylate, and the like;

nitroimidazolidine derivatives; N-cyanoamidine derivatives such as acetamiprid, and the like; chlorinated hydrocarbon compounds such as endosulfan, γ-BHC, 1,1-bis(chlorophenyl)-2,2,2-trichloroethanol, and the like; benzoylphenylurea compounds such as chlorfluazuron, teflubenzuron, flufenoxuron, and the like; phenylpyrazole compounds; methoxadiazon; bromopropylate; tetradifon; chinomethionate; pyridaben; fenpyroximate; diafenthiuron; tebufenpyrad; polynactin complex [tetranactin, dinactin, trinactin]; pyrimidifen; milbemectin; abamectin; ivermectin; and azadirachtin.

Examples of the repellent include 3,4-caranediol, N,N-diethyl-m-toluamide, 1-methylpropyl 2-(2-hydroxyethyl)-1-piperidinecarboxylate, p-menthane-3,8-diol, botanical essential oils such as hyssop oil, and the like.

Examples of the synergist include bis-(2,3,3,3-tetrachloropropyl)ether (S-421), N-(2-ethylhexyl) bicyclo[2.2.1]hept-5-ene-2,3-dicarboxylmide (MGK-264), and A-[2-(2-butoxyethoxy)ethoxy]-4,5-methylenedioxy-2-propyltoluene (piperonyl butoxide).

Hereinafter, the present invention will be further explained in more detail by Production Examples, Formulation Examples and Test Examples, but the present invention is not limited to these Examples.

First, Production Examples of the present invention will be shown.

Production Example 1

Under a nitrogen atmosphere, 0.59 g of N,N-dicyclohexyl carbodiimide was added to a mixture of 0.55 g of 4-methyl-2,3,5,6-tetrafluorobenzyl alcohol, 0.51 g of (1R)-trans-3-(2-cyano-1-propenyl)-2,2-dimethylcyclopropanecarboxylic acid, 0.10 g of 4-dimethylaminopyridine and 7 ml of anhydrous dichloromethane, and the mixture was stirred at room temperature for 3 hours. Thereafter, the reaction mixture was filtered, and the filtrate was concentrated under reduced pressure. The resulting residue was subjected to silica gel column chromatography to obtain 0.72 g of 4-methyl-2,3,5,6-tetrafluorobenzyl (1R)-trans-3-(2-cyano-1-propenyl)-2,2-dimethylcyclopropanecarboxylate represented by the following formula:

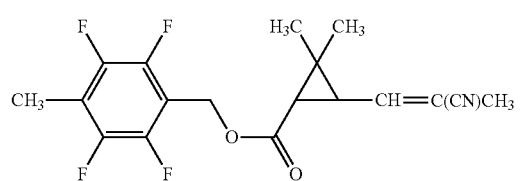

(A)

(ratio of isomers regarding double bond: Z/E=about 2/1) (hereinafter, referred to as the present compound (1)).

$^1$H-NMR (CDCl$_3$, TMS) δ (ppm): 1.21 (s, 3H, Z+E isomers), 1.32 (s, 3H, Z+E isomers), 1.71 (t, 1H, Z+E isomers), 1.95 (s, 3H, Z+E isomers), 2.19 (m, 1/3H, E isomer), 2.29 (s, 3H, Z+E isomers), 2.45 (m, 2/3H, Z isomer), 5.24 (s, 2H, Z+E isomers), 5.78 (d, 2/3H, Z isomer), 6.00 (d, 1/3H, E isomer)

Production Example 2

Under a nitrogen atmosphere, 0.49 g of N,N-dicyclohexylcarbodiimide was added to a mixture of 0.50 g of 4-methoxy-2,3,5,6-tetrafluorobenzyl alcohol, 0.43 g of (1R)-trans-3-(2-cyano-1-propenyl)-2,2-dimethylcyclopropanecarboxylic acid, 0.087 g of 4-dimethylaminopyridine and 7 ml of anhydrous dichloromethane, and the mixture was stirred at room temperature for 3 hours. Thereafter, the reaction mixture was filtered, and the filtrate was concentrated under reduced pressure. The resulting residue was subjected to silica gel column chromatography to obtain 0.62 g of 4-methoxy-2,3,5,6-tetrafluorobenzyl (1R) trans-3-(2-cyano-1-propenyl)-2,2-dimethylcyclopropanecarboxylate represented by the following formula:

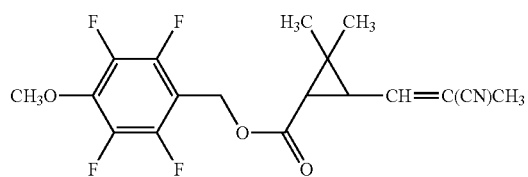

(ratio of isomers regarding double bond: Z/E=about 2/1) (hereinafter, referred to as the present compound (2)).

$^1$H-NMR (CDCl$_3$, TMS) δ (ppm): 1.21 (s, 3H, Z+E isomers), 1.31 (s, 3H, Z+E isomers), 1.72 (t, 1H, Z+E isomers), 1.96 (s, 3H, Z+E isomers), 2.19 (m, 1/3H, E isomer), 2.46 (m, 2/3H, Z isomer), 4.11 (s, 3H, Z+E isomers), 5.20 (s, 2H, Z+E isomers), 5.77 (d, 2/3H, Z isomer), 6.00 (d, 1/3H, E isomer)

Production Example 3

Under a nitrogen atmosphere, 0.23 g of 1-(3-dimethylaminopropyl)-3-ethylcarbodiimide hydrochloride was added to a mixture of 0.20 g of 4-allyl-2,3,5,6-tetrafluorobenzyl alcohol, 0.16 g of (1R)-trans-3-(2-cyano-1-propeny)-2,2-dimethylcyclopropanecarboxylic acid, 0.05 g of 4-dimethylaminopyridine and 4 ml of anhydrous chloroform, and the mixture was stirred at room temperature for 3 hours. Thereafter, the reaction mixture was poured into ice water, followed by extraction with ethyl acetate two times. Ethyl acetate layers were combined, washed with an aqueous saturated sodium chloride solution, dried with anhydrous sodium sulfate, and concentrated under reduced pressure. The resulting residue was subjected to silica gel column chromatography to obtain 0.32 g of 4-allyl-2,3,5,6-tetrafluorobenzyl (1R)-trans-3-(2-cyano-1-propenyl)-2,2-dimethylcyclopropanecarboxylate represented by the following formula:

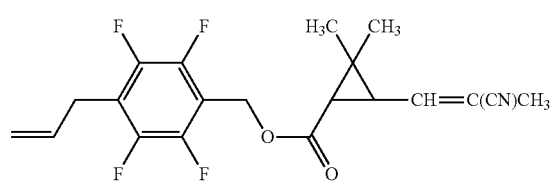

(ratio of isomers regarding double bond: Z/E=about 2/1) (hereinafter, referred to as the present compound (3)).

$^1$H-NMR (CDCl$_3$, TMS) δ (ppm): 1.23 (s, 3H, Z+E isomers), 1.35 (s, 3H, Z+E isomers), 1.71 (t, 1H, Z+E isomers), 1.97 (s, 3H, Z+E isomers), 2.20 (m, 1/3H, E isomer), 2.46 (m, 2/3H, Z isomer), 3.49 (m, 2H, Z+E isomers), 5.10 (m, 2H, Z+E isomers), 5.23 (s, 2H, Z+E isomers), 5.79 (d, 2/3H, Zisomer), 5.88 (m, 1H, Z+E isomers), 6.00 (d, 1/3H, E isomer)

Then, Formulation Examples will be shown. All the "parts" are by weight.

Preparation Example 1

Each 20 parts of the present compounds (1) to (3) is dissolved in 65 parts of xylene, 15 parts of Sorpol 3005X (registered trademark of Toho Chemical Industry Co., LTD.) is added thereto, and the resultant mixture is stirred and thoroughly mixed to obtain an emulsifiable concentrate.

Formulation Example 2

To each 40 parts of the present compounds (1) to (3) is added 5 parts of Sorpol 3005X, and the resulting mixture is thoroughly mixed. To the mixture are added 32 parts of CARPLEX #80 (synthetic hydrous silicon oxide, registered trademark of Shionogi & Co., Ltd.) and 23 parts of 300 mesh diatomaceous earth. The resulting mixture is stirred and mixed with a juice mixer to obtain a wettable powder.

Formulation Example 3

Each 1.5 parts of the present compounds (1) to (3), 1 part of TOKUSIL GUN (Synthetic hydrous silicon oxide, manufactured by Tokuyama Corp.), 2 parts of REAX 85A (sodium ligninsulfonate, manufactured by Westvaco chemicals), 30 parts of Bentonite FUJI (bentonite, manufactured by HOJUN Co., Ltd.) and 65.5 parts of SHOKOZAN A Clay (kaolin clay, manufactured by Shokozan Kogyosho Co.) are ground and thoroughly mixed. Water is added thereto, and the mixture is thoroughly kneaded, granulated with an extrusion granulator, and dried to obtain 1.5% granules.

Formulation Example 4

Each 10 parts of the present compounds (1) to (3), 10 parts of phenylxylylethane and 0.5 parts of SUMIDUR L-75 (tolylenediisocyanate, manufactured by Sumika Bayer Urethane Co., Ltd) are mixed. The resulting mixture is added to 20 parts of a 10% aqueous gum arabic solution, followed by stirring with a homomixer to obtain an emulsion of an average particle diameter of 20 µm. To the emulsion, 2 parts of ethylene glycol is added, and the mixture is further stirred in a warm bath at 60° C. for 24 hours to obtain a microcapsule slurry. Separately, 0.2 part of xanthan gum and 1.0 part of VEEGUM R (aluminum magnesium silicate, manufactured by Sanyo Chemical Industries, Ltd.) are dispersed in 56.3 parts of ion-exchanged water to obtain a thickener solution. Then, 42.5 parts of the microcapsule slurry and 57.5 parts of the thickener solution are mixed to obtain microencapsulated formulation.

Formulation Example 5

Each 10 parts of the present compounds (1) to (3) and 10 parts of phenylxylylethane are mixed, and the mixture is added to 20 parts of a 10% aqueous polyethylene glycol solution, followed by stirring with a homomixer to obtain an emulsion of an average particle diameter of 3 µm. Separately, 0.2 parts of xanthan gum and 1.0 part of VEEGUM R (aluminum magnesium silicate, manufactured by Sanyo Chemical Industries, Ltd.) are dispersed in 58.8 parts of ion-exchanged water to obtain a thickener solution. Then, 40 parts of the emulsion solution and 60 parts of the thickener solution are mixed to obtain a flowable formulation.

Formulation Example 6

To each 5 parts of the present compounds (1) to (3) are added 3 parts of CARPLEX #80 (synthetic hydrous silicon oxide fine powder, registered trademark of Shionogi & Co., Ltd.), 0.3 parts of PAP (mixture of monoisopropyl phosphate and diisopropyl phosphate) and 91.7 parts of talc (300 mesh), and the mixture is stirred and mixed with a juice mixer to obtain a dust.

Formulation Example 7

Each 0.1 parts of the present compounds (1) to (3) is dissolved in 10 parts of dichloromethane, and the solution is mixed with 89.9 parts of deodorized kerosene to obtain an oil solution.

Formulation Example 8

Each 1 part of the present compounds (1) to (3), 5 parts of dichloromethane and 34 parts of deodorized kerosene are mixed and dissolved, and filled into an aerosol container. After a valve part is attached, 60 parts of a propellant (liquefied petroleum gas) is filled under pressure through the valve part to obtain an oily aerosol.

Formulation Example 9

A solution obtained by mixing and dissolving each 0.6 parts of the present compounds (1) to (3), 5 parts of xylene, 3.4 parts of a deodorized kerosene and 1 part of ATMOS 300 (emulsifier, registered trademark of Atlas Chemical Co.), and 50 parts of water are filled into an aerosol container, and 40 parts of a propellant (liquefied petroleum gas) is filled under pressure through a valve part to obtain an aqueous aerosol.

Formulation Example 10

Each 0.3 g of the present compounds (1) to (3) is dissolved in 20 ml of acetone, the solution and 99.7 g of a base material for a coil (obtained by mixing Tabu powder, Pyrethrum marc and wooden powder at ratio of 4:3:3) are uniformly stirred and mixed, 100 ml of water is added thereto, and the mixture is thoroughly kneaded, molded, and dried to obtain an insecticidal coil.

Formulation Example 11

Acetone is added to each 0.8 g of the present compounds (1) to (3) and 0.4 g of piperonyl butoxide to dissolve them and the total volume is adjusted to 10 ml. A base material for insecticidal mat for electric heating (fibrils of a mixture of cotton linter and pulp are hardened in the shape of a plate) of 2.5 cm×1.5 cm having a thickness of 0.3 cm is uniformly impregnated with 0.5 ml of this solution to obtain an insecticidal mat for electric heating.

Formulation Example 12

Each 3 parts of the present compounds (1) to (3) is dissolved in 97 parts of deodorized kerosene to obtain a solution, which is placed into a container made of polyvinyl chloride, and an absorptive wick (obtained by solidifying inorganic powder with binder, and calcining this) having an upper part which can be heated with a heater, is inserted to obtain a part used in an absorptive wick type electric heating fumigation device.

Formulation Example 13

Each 100 mg of the present compounds (1) to (3) is dissolved in a suitable amount of acetone, and a 4.0 cm×4.0 cm porous ceramic plate having a thickness of 1.2 cm is impregnated with the solution to obtain a heating fumigant.

Formulation Example 14

Each 100 μg of the present compounds (1) to (3) is dissolved in a suitable amount of acetone, the solution is uniformly applied on a 2 cm×2 cm filter having a thickness of 0.3 mm, and acetone is air-dried to obtain a volatile agent for using at room temperature.

Then, Test Examples demonstrate that the present compound is effective as an active ingredient of a pest controlling agent.

Test Example 1

Each 0.025 part of the present compounds (1) to (3) produced in the above Production Examples was dissolved in 10 parts of dichloromethane, and the solution was mixed with 89.975 parts of deodorized kerosene to prepare a 0.025% oil solution.

Adult houseflies (5 males and 5 females, total 10) were released in a cubic chamber having each side of 70 cm, and 0.7 ml of the 0.025% oil solution of the present compound prepared above was sprayed into the chamber through a small window on a side of the chamber using a spraying gun at a pressure of $8.8 \times 10^4$ Pa. Two minutes after spraying, the number of knocked-down houseflies was counted (2 repetitions).

In addition, the same as above test was performed by using, in place of the present compounds (1) to (3), 4-methyl-2,3,5,6-tetrafluorobenzyl (1R)-trans-3-(2-methyl-1-propenyl)-2,2-dimethylcyclopropanecarboxylate represented by the formula:

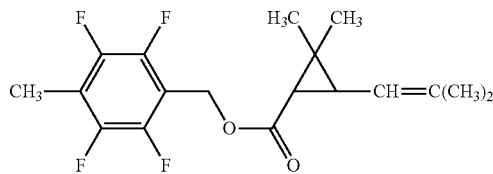

(compound described in EP0926129A1; hereinafter, referred to as Comparative Compound (1)), 4-methoxy-2,3,5,6-tetrafluorobenzyl (1R)-trans-3-(2-methyl-1-propenyl)-2,2-dimethylcyclopropanecarboxylate represented by the following formula:

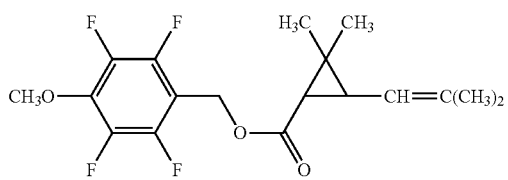

(compound described in U.S. Pat. No. 4,405,640; hereinafter, referred to as Comparative Compound (2)), and 4-allyl-2,3,5,6-tetrafluorobenzyl (1R)-trans-3-(2-methyl-1-propenyl)-2,2-dimethylcyclopropanecarboxylate represented by the following formula:

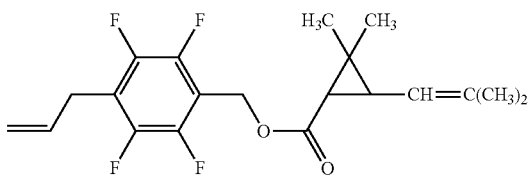

(compound described in U.S. Pat. No. 4,405,640; hereinafter, referred to as Comparative compound (3)) as controls.

The results are shown in Table 1.

TABLE 1

| Test compound | Number of knock-down houseflies |
| --- | --- |
| Present compound (1) | 10 |
| Present compound (2) | 10 |
| Present compound (3) | 9 |
| Comparative compound (1) | 0 |
| Comparative compound (2) | 0 |
| Comparative compound (3) | 0 |

Test Example 2

Each 0.00625 parts of the present compounds (1) to (3) produced in the above production Examples was dissolved in 10 parts of dichloromethane, and the solution was mixed with 89.99375 parts of deodorized kerosene to prepare a 0.00625% oil solution.

Ten common mosquito (*Culex pipens pallens*) females were released in a cubic chamber having each side of 70 cm, and 0.7 ml of the 0.00625% oil solution of the present compound prepared above was sprayed into the chamber through a small window on a side of the chamber using a spraying gun at a pressure of $8.8 \times 10^4$ Pa. After ten minutes, common mosquito females were recovered in a clean cup (bottom diameter 8.2 cm) with a cotton wool containing a 0.5% aqueous sugar, and allowed to stand until the next day. After 24 hours, the number of dead mosquitoes was counted, and a mortality was calculated (2 repetition).

In addition, the same as above test was performed using, in place of present compounds (1) to (3), 4-methoxymethyl-2,3,5,6-tetrafluorobenzyl (1R)-trans-3-(2-cyano-1-propenyl)-2,2-dimethylcyclopropanecarboxylate (ratio of isomers regarding double bond: Z/E=about 2/1; compound described in U.S. Pat. No. 6,908,945B2; hereinafter refereed to as Comparative Compound (4)) as a control.

The results are shown in Table 2.

TABLE 2

| Test compound | Mortality (%) |
| --- | --- |
| Present compound (1) | 95 |
| Present compound (2) | 100 |
| Present compound (3) | 70 |
| Comparative compound (4) | 16 |

INDUSTRIAL APPLICABILITY

Since the present compound has an excellent pest controlling efficacy, it is useful as an active ingredient of a pest controlling agent.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. An ester compound represented by the formula (1):

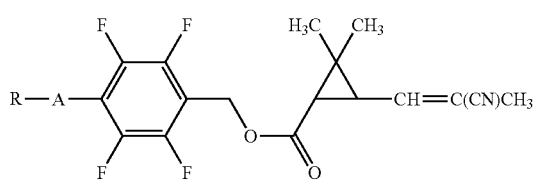

wherein R represents a C1-C4 alkyl group or a C3-C4 alkenyl group, and A represents an oxygen atom.

2. A pest controlling agent comprising the ester compound according to claim 1 as an active ingredient.

3. A method for controlling pests comprising applying an effective amount of the ester compound according to claim 1 to the pests or a place where the pests inhabit.

4. The ester compound according to claim 1, wherein R represents a C1-C4 alkyl group.

5. A pest controlling agent comprising the ester compound according to claim 4 as an active ingredient.

6. A method for controlling pests comprising applying an effective amount of the ester compound according to claim 4 to the pests or a place where the pests inhabit.

7. The ester compound according to claim 1, wherein R represents a C3-C4 alkenyl group.

8. A pest controlling agent comprising the ester compound according to claim 7 as an active ingredient.

9. A method for controlling pests comprising applying an effective amount of the ester compound according to claim 7 to the pests or a place where the pests inhabit.

* * * * *